US011459299B2

(12) United States Patent
Cooks et al.

(10) Patent No.: US 11,459,299 B2
(45) Date of Patent: *Oct. 4, 2022

(54) CONDUCTING REACTIONS IN LEIDENFROST-LEVITATED DROPLETS

(71) Applicant: Purdue Research Foundation, West Lafayette, IN (US)

(72) Inventors: Robert Graham Cooks, West Lafayette, IN (US); Christopher Pulliam, West Lafayette, IN (US); Ryan M. Bain, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/993,553

(22) Filed: Aug. 14, 2020

(65) Prior Publication Data
US 2021/0053921 A1 Feb. 25, 2021

Related U.S. Application Data

(63) Continuation of application No. 15/613,520, filed on Jun. 5, 2017, now Pat. No. 10,774,044.

(60) Provisional application No. 62/346,594, filed on Jun. 7, 2016, provisional application No. 62/346,213, filed on Jun. 6, 2016.

(51) Int. Cl.
| | |
|---|---|
| *C07D 213/04* | (2006.01) |
| *C07D 209/40* | (2006.01) |
| *C07J 41/00* | (2006.01) |
| *C07C 45/72* | (2006.01) |

(52) U.S. Cl.
CPC ............ *C07D 213/04* (2013.01); *C07C 45/72* (2013.01); *C07D 209/40* (2013.01); *C07J 41/0005* (2013.01)

(58) Field of Classification Search
CPC .... C07D 213/04; C07D 209/40; C07C 45/72; C07J 41/0005
See application file for complete search history.

(56) References Cited

U.S. PATENT DOCUMENTS

| | | | |
|---|---|---|---|
| 5,644,131 | A | 7/1997 | Hansen |
| 6,838,666 | B2 | 1/2005 | Ouyang et al. |
| 7,335,897 | B2 | 2/2008 | Takats et al. |
| 7,361,311 | B2 | 4/2008 | Cooks et al. |
| 8,304,718 | B2 | 11/2012 | Ouyang et al. |
| 8,410,431 | B2 | 4/2013 | Ouyang et al. |
| 9,184,038 | B2 | 11/2015 | Cooks et al. |
| 9,500,623 | B2 | 11/2016 | Cooks et al. |

FOREIGN PATENT DOCUMENTS

WO 2009/102766 A1 8/2009

OTHER PUBLICATIONS

Abdelaziz, 2013, Green chemistry and nanofabrication in a levitated Leidenfrost drop, Nat. Commun., 4:2400.
Bain, 2014, Mass Spectrometry in Organic Synthesis: Claisen-Schmidt Base-Catalyzed Condensation and Hammett Correlation of Substituent Effects, J. Chem. Educ., vol. 91: pp. 1985-1989.
Bain, 2015, Accelerated Hantzsch electrospray synthesis with temporal control of reaction intermediates, Chem. Sci., vol. 6:397-401.
Banerjee, 2015, Syntheses of Isoquinoline and Substituted Quinolines in Charged Microdroplets, Angew. Chem. Int. Ed., vol. 54: pp. 14795-14799.
Bonner, 1977, The Cylindrical Ion Trap, International Journal of Mass Spectrometry and Ion Physics, 24(3):255-269.
Carroll, 1975, Atmospheric Pressure Ionization Mass Spectrometry: Corona Discharge Ion Source for Use in Liquid Chromatograph-Mass Spectrometer-Computer Analytical System, Anal. Chem. 47:2369-2373.
Cech, 2001, Practical Implications of Some Recent Studies in Electrospray Ionization Fundamentals, Mass Spectrom. Rev., vol. 20: pp. 362-387.
Cody, 2005, Versatile new ion source for the analysis of materials in open air under ambient conditions, Anal. Chem., 71, 2297-2302.
Cotte-Rodriguez, 2006, Non-proximate detection of explosives and chemical warfare agent simulants by desorption electrospray ionization mass spectrometry, 2968-2970.
Fenn, 1989, Electrospray ionization for mass spectrometry of large biomolecules, Science, 246:64-71.
Gao, 2008, Design and characterization of a multisource hand-held tandem mass spectrometer, Anal. Chem. 80:7198-7205.
Girod, 2011, Accelerated bimolecular reactions in microdroplets studied by desportion electrospray ionization mass spectrometry, Chem. Sci., vol. 2: pp. 501-510.
Grimm, 2005, Dynamics of Field-Induced Droplet Ionization: Time-Resolved Studies fo Distrortion, Jetting, and Progeny Formation from Charged and Neutral Methanol Droplets Exposed to Strong Electric Field, J. Phys. Chem. B, vol. 109: pp. 8244-8250.
Grimm, 2006, Probing Interfacial Chemistry of Single Droplets with Field-Induced Droplet Ionization Mass Spectrometry: Physical Adsorption of Polycyclic Aromatic Hydrocarbons and Ozonolysis of Oleic Acid and Related Compounds, Anal. Chem., vol. 78: pp. 3800-3806.
Hagar, 2002, A new linear ion trap mass spectrometer, Rapid Communications in Mass Spectrometry, 16(6):512-526.
Hou, 2011, Sampling wand for an ion trap mass spectrometer, Anal. Chem., 83:1857-1861.
Kazachkov, Heat transfer and dynamics of the droplet on a superheated surface, WSEAS Trans. Heat Mass Transf., vol. 7: pp. 47-57.
Kogelschatz, 2003, Plasma Chemistry and Plasma Processing, 23:1-46.
Konermann, 2013, Unraveling the Mechanism of Electrospray Ionization, Anal. Chem., vol. 85: pp. 2-9.
Laiko, 2000, Atmospheric pressure matrix-assisted laser desorption/ionization mass spectrometry, Anal. Chem., 72:652-657.

(Continued)

Primary Examiner — Barbara P Badio
(74) Attorney, Agent, or Firm — Brown Rudnick LLP; Adam M. Schoen

(57) ABSTRACT

The invention generally relates to conducting reactions in Leidenfrost-levitated droplets.

18 Claims, 11 Drawing Sheets

(56) References Cited

OTHER PUBLICATIONS

Lee, 2015, Imagining Dirac-mass disorder from magnetic dopant atoms in the ferromagnetic topological insulator Crx (Bi0.1 Sb0.9)2-x Te3, Proc. Natl. Acad. Sci., 11(5):1316-1321.

Lee, 2015, Straightforward Synthesis of Metal Nanoparticles and Hierarchical porous Metals Assisted by Partial Film Boing Phenomena, Chem. Mater., vol. 27: pp. 5151-5160.

Macky, 1931, Some Investigations on the Deformation and Breaking of Water Drops in Strong Electric Fields, Proc. R. Soc. A., 133: 565-587.

Muller, 2012, Accelerated Carbon-Carbon Bond-Forming Reactions in Preparative Electrospray, Agnew Chem. Int. Ed., vol. 51: pp. 11832-11835.

Quere, 2013, Leidenfrost Dynamics, Annu. Rev. Fluid Mech., vol. 45: pp. 197-215.

Shiea, 2005, Electrospray-assisted laser desorption/ionization mass spectrometry for direct ambient analysis of solids, J. Rapid Communications in Mass Spectrometry, 19:3701-3704.

Sokol et al., 2011, Miniature mass spectrometer equipped with electrospray and desorption electrospray ionization for direct analysis of organics from solids and solutions, Int. J. Mass Spectrum. 306:187-195.

Takats, 2004, Mass Spectrometry Sampling Under Ambient Conditions with Desorption Electrospray Ionization, Science, 306:471-473.

Tanaka, 1988, Protein and polymer analyses up to m/z 100 000 by laser ionization time-of-flight mass spectrometry, Rapid Commun. Mass Spectrom., 2:151-153.

Wilson, 1920, Investigations on Lightning Discharges and on the Electric Field of Thunderstorms, Philos. Trans. pp. 73-115.

Wilson, 1925, The bursting of soap-bubbles ina uniform electric field, Proc. Cambridge Philos. Soc., 22:728-730.

Yamashita, 1984, Electrospray Ion Source. Another Variation on the Free-Jet Theme, J. Phys. Chem., 88:4451-4459.

Yan, 2013, Chemical Reactivity Assessment Using Reactive Paper Spray Ionization Mass Spectrometry: The Katritzky Reaction, Chempluschem, vol. 78: pp. 1142-1148.

Yan, 2016, Organic Reactions in Microdroplets: Reaction Acceleration Revealed by Mass Spectrometry, Angew. Chemie Int. Ed. 55(42):12960-12972.

CONDUCTING REACTIONS IN LEIDENFROST-LEVITATED DROPLETS

RELATED APPLICATIONS

The present application is a continuation of U.S. nonprovisional application Ser. No. 15/613,520, filed Jun. 5, 2017, which claims the benefit of and priority to U.S. provisional application Ser. No. 62/346,594, filed Jun. 7, 2016, and U.S. provisional application Ser. No. 62/346,213, filed Jun. 6, 2016, the content of each of which is incorporated by reference herein in its entirety.

GOVERNMENT INTEREST

This invention was made with government support under DE-FG02-06ER15807 awarded by the U.S. Department of Energy and CHE-1307264 awarded by the National Science Foundation. The government has certain rights in the invention.

FIELD OF THE INVENTION

The invention generally relates to conducting reactions in Leidenfrost-levitated droplets.

BACKGROUND

Electrospray ionization (ESI) is a commonly used ionization technique for mass spectrometry (MS) in which analyte ions are generated and effectively transported from solution phase to the gas phase. In ESI, analytes in a charged solution are sprayed pneumatically to produce a plume of charged microdroplets. These microdroplets undergo desolvation and coulombic fission events to produce numerous smaller and more concentrated droplets. These microdroplets are the nexus for accelerated chemical reactions.

On-line monitoring experiments have demonstrated that increasing a distance between the sprayer and a mass spectrometer inlet increases a product to starting material ratio. It has been demonstrated that reaction rate acceleration in spray (compared to bulk) for the Pomeranz-Fritsch synthesis of isoquinoline was greater than six orders of magnitude. In a study of the Claisen-Schmidt base-catalyzed condensation, it was shown that acceleration is not simply a result of increased concentration dependence but is strongly influenced by interfacial effects. Successful efforts at milligram scale chemical synthesis using reactions in electrosprayed droplets have been reported.

SUMMARY

The invention provides a new approach for accelerating chemical reactions. Aspects of the invention take advantage of the Leidenfrost effect. The Leidenfrost effect occurs when a liquid is brought to a surface heated to a temperature significantly higher than the liquid's boiling point. As the droplet approaches the super-heated surface, an insulating vapor layer is formed that keeps the solution from boiling rapidly. With this vapor cushion in place, the droplet levitates on the surface and solvent gradually evaporates. The methods of the invention use the Leidenfrost effect to perform accelerated chemical reactions in droplets. In certain embodiments, the reaction is conducted while maintaining a substantially constant volume of the droplets. By maintaining Leidenfrost droplets at constant volume is it shown that acceleration is mainly due to interfacial effects.

In other embodiments, the droplet reduces in volume as the reaction occurs and the reaction product is formed in a Leidenfrost droplet having a reduced volume. The ability to multiplex Leidenfrost microreactors and to use them to synthesize milligram quantities of reaction product is also demonstrated.

In certain aspects, the invention provides methods for forming a reaction product that involve conducting a reaction within a Leidenfrost-levitated droplet while maintaining a substantially constant volume of the Leidenfrost-levitated droplet, thereby forming a reaction product within the Leidenfrost-levitated droplet. Maintaining the substantially constant volume may involve introducing droplets of pure solvent or the reaction mixture to the Leidenfrost-levitated droplet. A rate at which the droplets of pure solvent or the reaction mixture are introduced to the Leidenfrost-levitated droplet may depend on an evaporation rate of the Leidenfrost-levitated droplet. In certain embodiments, the methods are conducted without the use of surfactants.

The methods of the invention may further involve conducting multiple reactions in multiple separate Leidenfrost-levitated droplets. In certain embodiments, the multiple separate Leidenfrost-levitated droplets are merged with each other. The multiple reactions may be the same. Alternatively, the multiple reactions may be different.

Other aspects of the invention provide methods for forming a reaction product that involve introducing a first liquid droplet onto a heated surface that is at a temperate that is at or above a Leidenfrost point of the first liquid such that the first liquid droplet levitates on the heated surface. The first liquid droplet includes reagents for a reaction. A reaction is conducted in the first liquid droplet using the reagents in order to form a reaction product. The methods then involve introducing one or more subsequent liquid droplets to the first liquid droplet on the heated surface such that the one or more subsequent liquid droplets merge with the first liquid droplet. The one or more subsequent liquid droplets may include the reagents for the reaction or pure solvent or another type of liquid. In some embodiments the composition of the gas surrounding the Leidenfrost droplet may be adjusted so as to produce desired reactions.

In certain embodiments, the first liquid droplet is maintained at a substantially constant volume throughout the method. A rate at which the one or more subsequent liquid droplets are introduced to the first liquid droplet will depend on an evaporation rate of the first liquid droplet. In certain embodiments, the method is conducted without the use of surfactants.

The methods of the invention may further involve analyzing the reaction product. Analyzing may be by any method known in the art. An exemplary method for analysis uses a mass spectrometry technique.

Other aspects of the invention provide methods for forming a reaction product that involve conducting a reaction within a Leidenfrost-levitated droplet, thereby forming a reaction product within the Leidenfrost-levitated droplet. In certain embodiments, the droplet reduces in volume as the reaction occurs.

For the embodiments described above, a rate of the reaction may be accelerated as compared to a rate of the reaction conducted outside of the Leidenfrost-levitated droplet. The methods of the invention have many uses, and one exemplary use is performing degradation studies of commercial products like lubricants, cosmetics, foodstuffs, medicines, etc., in which a rate of the reaction, i.e. degradation, is accelerated within the Leidenfrost-levitated droplet as compared to a rate of the reaction conducted outside of the Leidenfrost-levitated droplet. The methods of the invention significantly cuts time for such studies. Additionally, the methods of the invention allow for multiplexing, which makes the methods especially useful in these sorts of product spoilage studies.

BRIEF DESCRIPTION OF THE DRAWINGS

FIGS. 3A-B show less product (10) vs. starting material (8) than do the corresponding Leidenfrost experiments in FIGS. 3C-D, which display acceleration factors of 50 and 8, respectively.

FIG. 4A shows 2 min bulk phase reaction showing 13/11 ratio. FIG. 4B shows Leidenfrost reaction showing an acceleration factor of 17. Addition of triton x-100 at 1% and 5% v/v suppresses the acceleration effect to a factor of just 2 and units as shown in FIGS. 4C-D, respectively. Ions with spacing of 44 are PEG spaced peaks of triton.

DETAILED DESCRIPTION

Leidenfrost-levitated droplets can be used to accelerate chemical reactions in processes that appear to be similar to reaction acceleration in charged microdroplets produced by electrospray ionization. Reaction acceleration in Leidenfrost droplets has been demonstrated for base-catalyzed Claisen-Schmidt condensations, hydrazone formation from pre-charged and neutral ketones and for Katritzky pyrylium to pyridinium conversion under various reaction conditions. Comparisons with bulk reactions and with reactions in electrosprayed microdroplets show intermediate values of acceleration factors (2-50). In certain embodiments, by maintaining Leidenfrost droplets at constant volume, it is shown that acceleration is mainly due to interfacial effects. Accelerated reactions are also conducted in which the volume of the Leidenfrost-levitated droplet is allowed to decrease. The ability to multiplex Leidenfrost microreactors and to use them to synthesize milligram quantities of reaction product is demonstrated.

Figure 1:
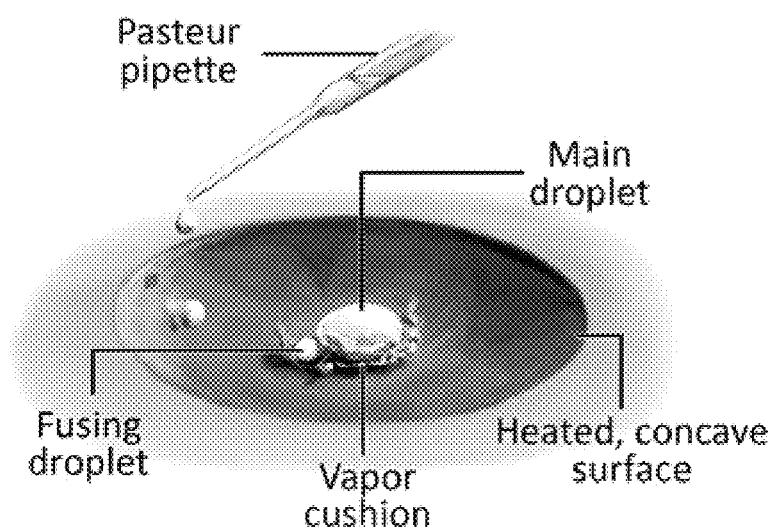
FIG. 1 shows a Leidenfrost reaction system used in methods of the invention in which additional reaction mixture is added via pipette to maintain constant volume Leidenfrost droplets. The added droplets impact the surface and fuse with the main levitated droplet which sits atop a cushion of solvent vapor.

In certain embodiments, Leidenfrost droplets were maintained at constant volume (ca. 0.5 mL) by adding approximately 2 mL of the reaction mixture over the course of droplet levitation (2 min) (FIG. 1). Because the droplets concentrate the reaction mixture by approximately 4 times over the initial concentration during the constant volume experiment, bulk-phase reactions were also performed at 4 fold higher concentration in order to correct for the concentration effect. Additional experiments were performed by maintaining constant volume with pure solvent and comparative bulk reactions were performed at room temperature at the initial concentrations used for the Leidenfrost experiments. These additional experiments helped separate effects of concentration changes from those associated with other features of the levitated droplets, notably interfacial effects.

Leidenfrost experiments were conducted for 2 min in a petri dish atop a heater/stirrer (Fisher Scientific) at a surface temperature between 400 and 540° C. All analyses were performed by nanoESI using an LTQ XL-Orbitrap hybrid mass spectrometer (Fisher Scientific, San Jose, Calif.) under conditions shown not to lead to reaction acceleration in the analysis step. Additional details on each reaction system studied can be found in Example 1 below. All reagents and solvents were purchased from Sigma-Aldrich (St. Louis, Mo.) unless otherwise specified. Discussion of the determination of the acceleration factor and the nESI-MS method of chemical analysis can be found in Examples 2 and 3 below.

Hydrazone formation between cortisone (1) and Girard's Reagent T (2) to form the pre-charged hydrazone product (3) (Scheme 1) was selected as a model reaction because a similar system had been characterized in the bulk-phase and using acceleration in desorption electrospray ionization (DESI) droplets. The results (Table 1) show significant reaction acceleration, expressed as an acceleration factor and defined as the ratio of the MS product ion signal to the reagent ion signal in the Leidenfrost vs. the ratio in the bulk experiment. Acceleration factors measuring the product/reagent ratios with the 5 mM bulk concentrations would be 17; however, the concentration increase in the Leidenfrost droplets due to evaporation must be taken into account. This was done by measuring the bulk reaction data measured at four times the initial concentration. Hydrazone formation from the Leidenfrost droplets then shows a product (3)/reagent (1) ion ratio which is notably higher (factor of 4) than that for the bulk solution (Example 4 below). Note that addition of acid increases product formation in both experiments. Note that in this experiment and those with other reactions, the product signals in Leidenfrost droplets after two minutes matched those reached after ca. 1 or more hours in the corresponding bulk experiment (Table 1).

Scheme 1: Cortisone (1) and Girard's reagent T (2) react to form the hydrazone product (3).

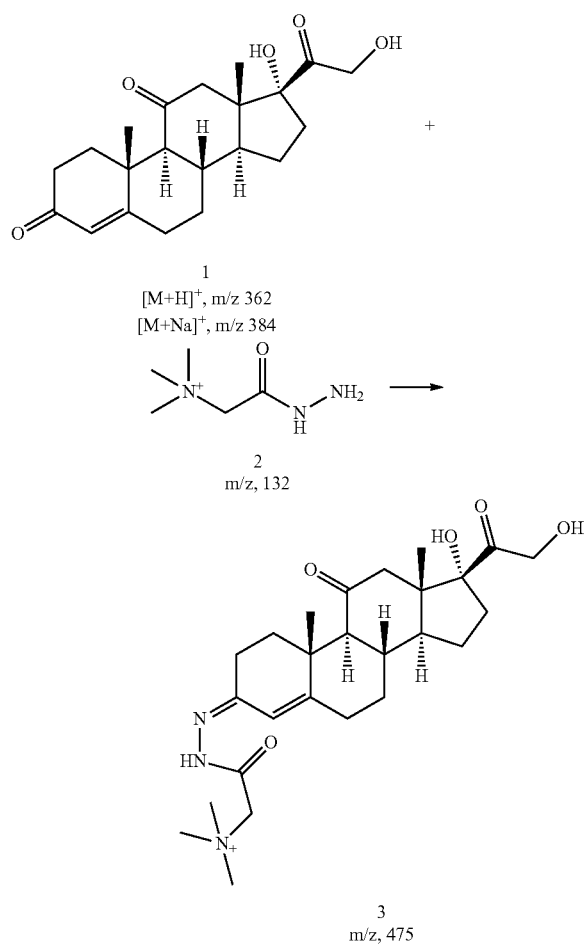

Figure 2A:
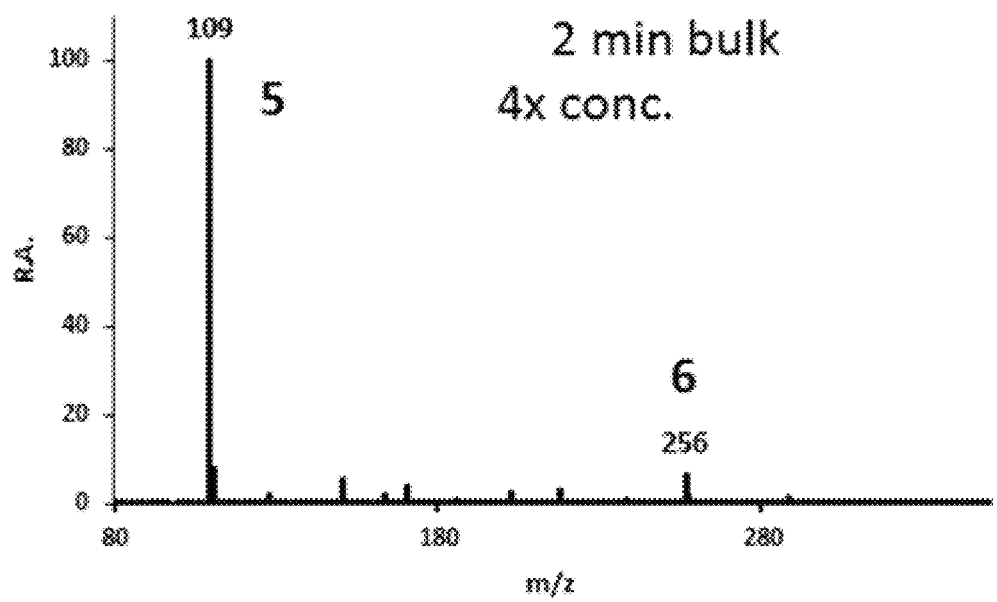
FIGS. 2A-B are spectra showing that bulk-phase reaction of 4 and 5 after 2 min showed mainly reagent 5 and some intermediate (6) while the parallel Leidenfrost experiment provided significant product (7) formation.
Figure 2B:
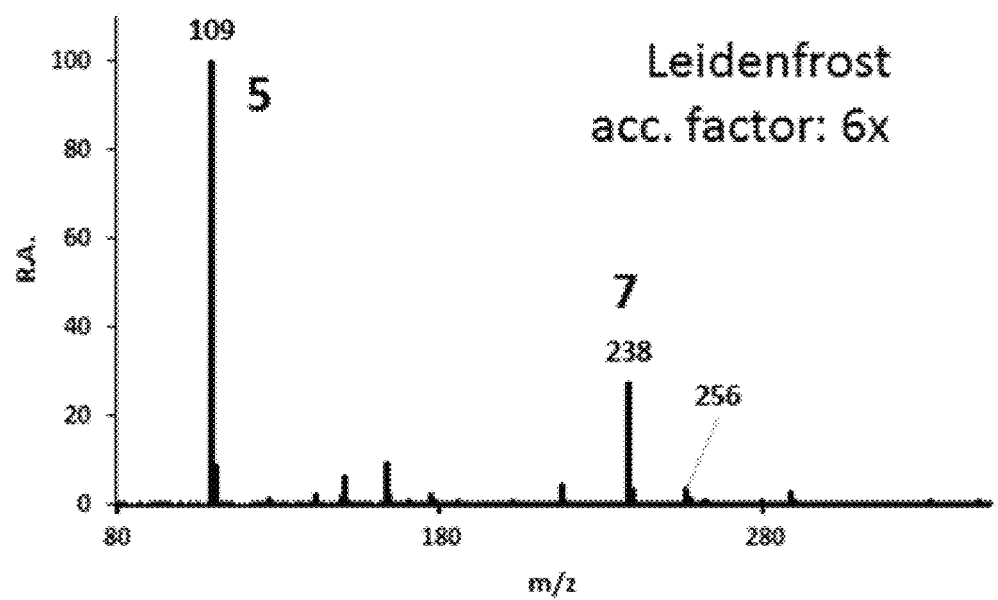
Figure 3A:
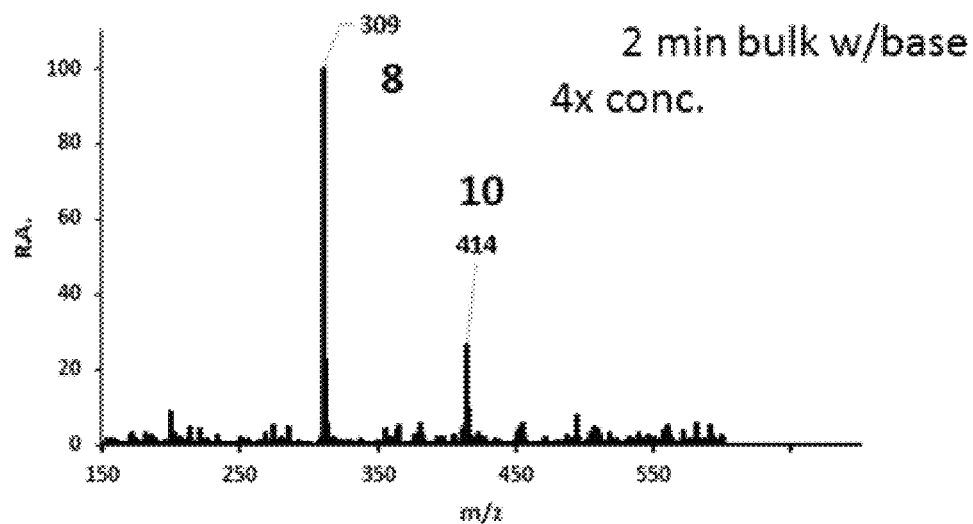
FIGS. 3A-B are spectra showing bulk-phase Katritsky reaction with and without base.
Figure 3B:
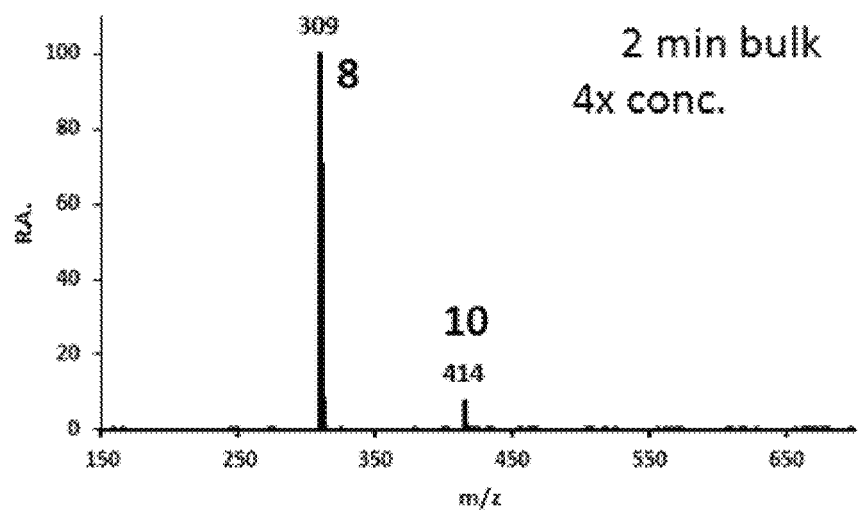
Figure 3C:
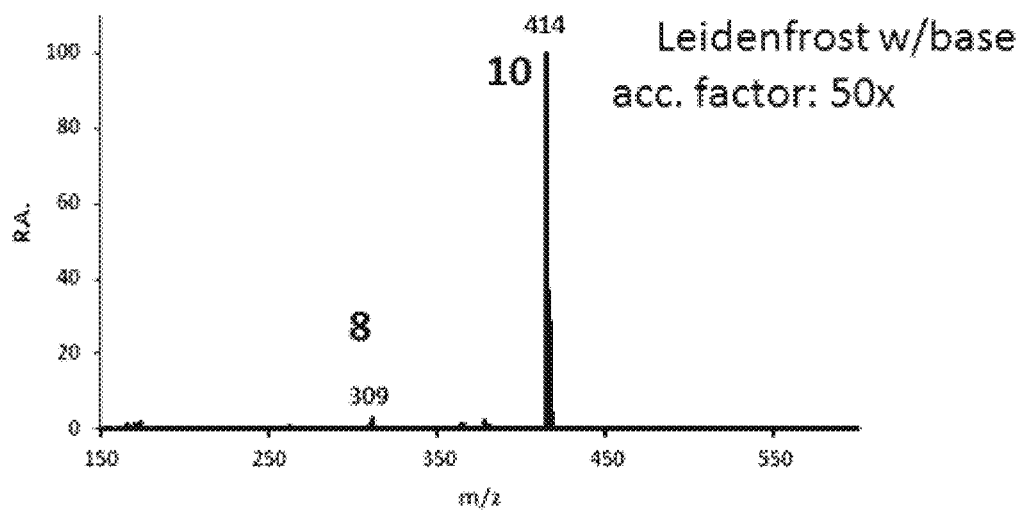
Figure 3D:
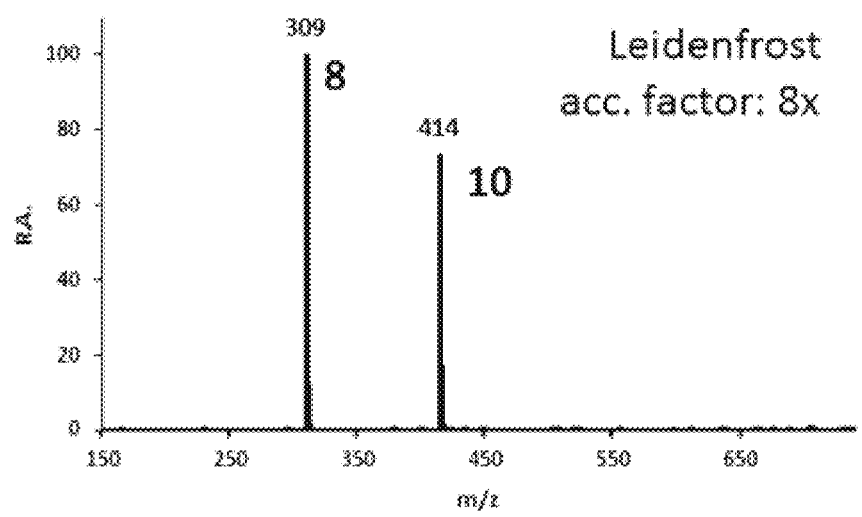
Figure 4A:
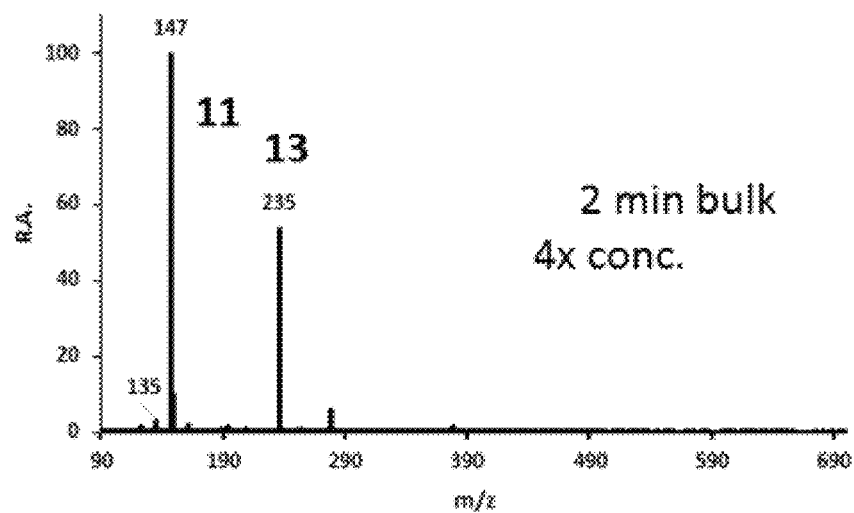
FIGS. 4A-D show surface effects in Claisen-Schmidt reactions.
Figure 4B:
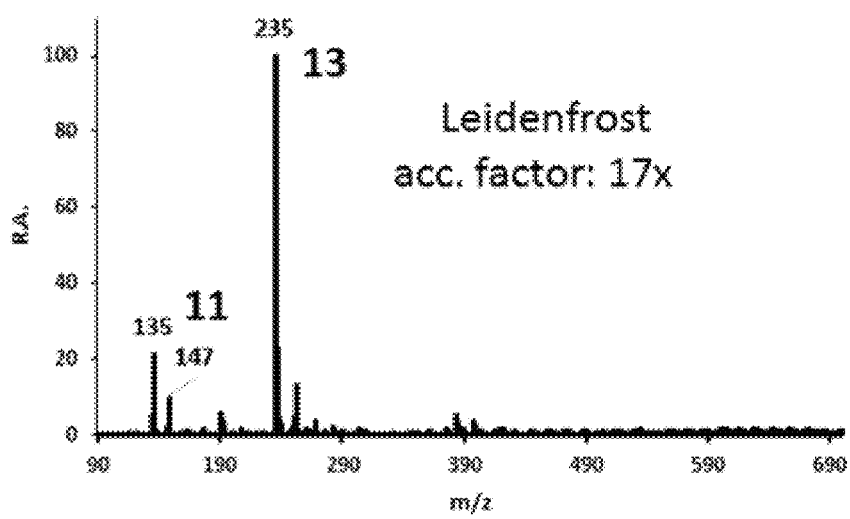
Figure 4C:
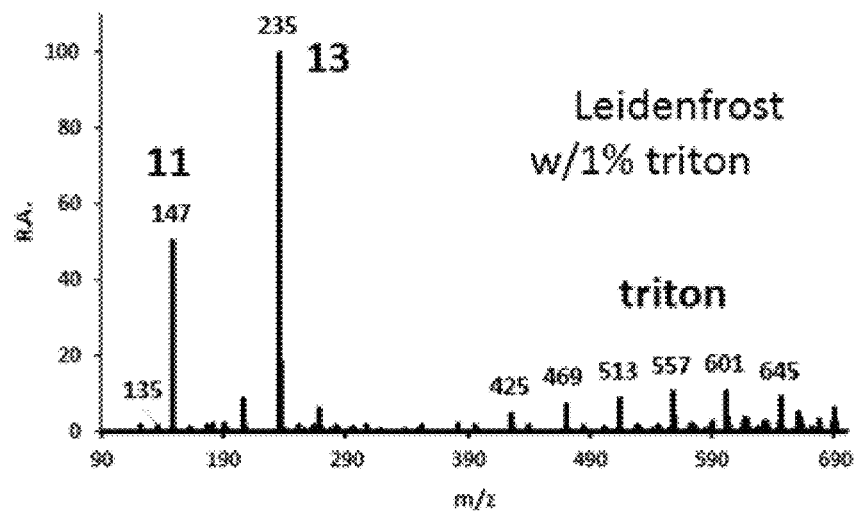
Figure 4D:
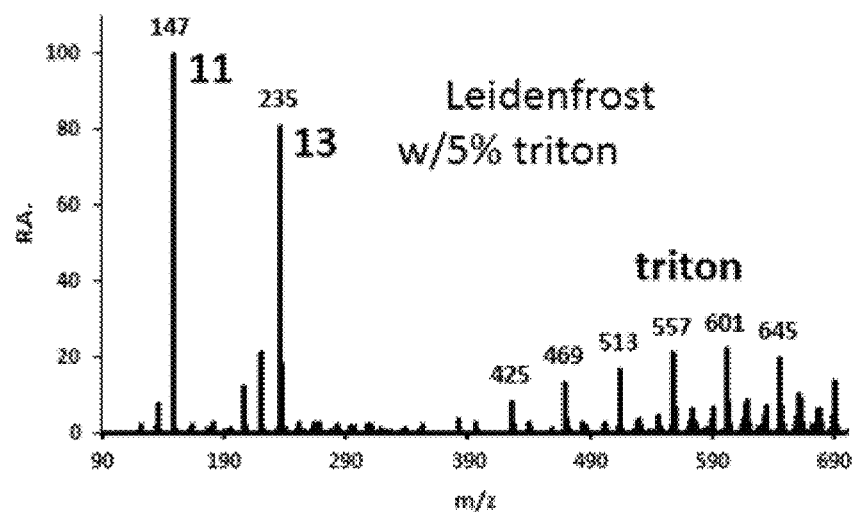
Figure 5A:
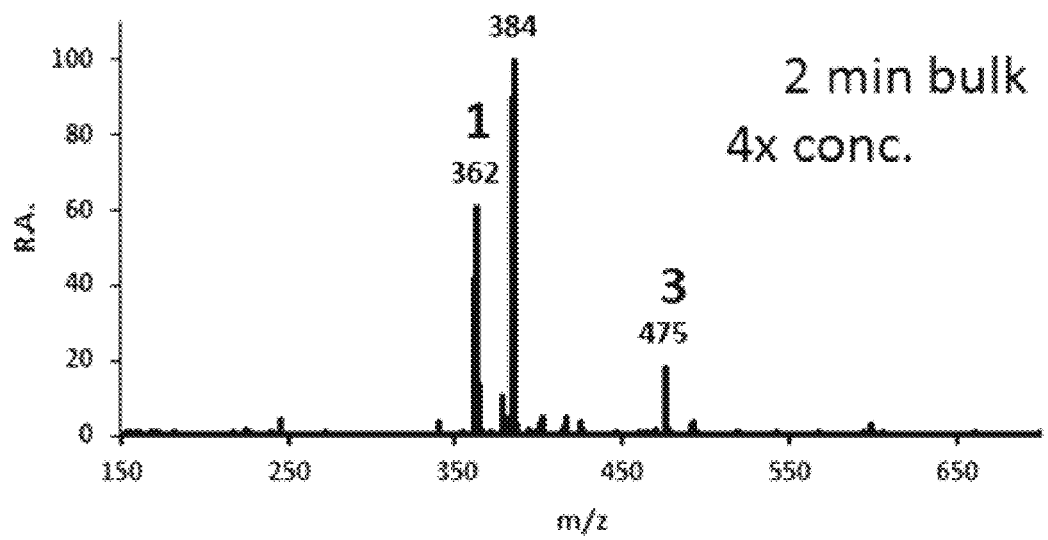
FIGS. 5A-D show Bulk-phase reaction without (FIG. 5A) and with additional acid (FIG. 5B) at 2 min reaction time shows significantly less reaction product than do the corresponding 2 min Leidenfrost droplet experiments (FIGS. 5C-D). Note that reagent appears as the protonated and the sodiated species (m/z 362 and m/z 384) and their sum was used to calculate the acceleration factor. Acid catalysis is responsible for the difference between FIGS. 5A and C and FIGS. 5B and D.
Figure 5B:
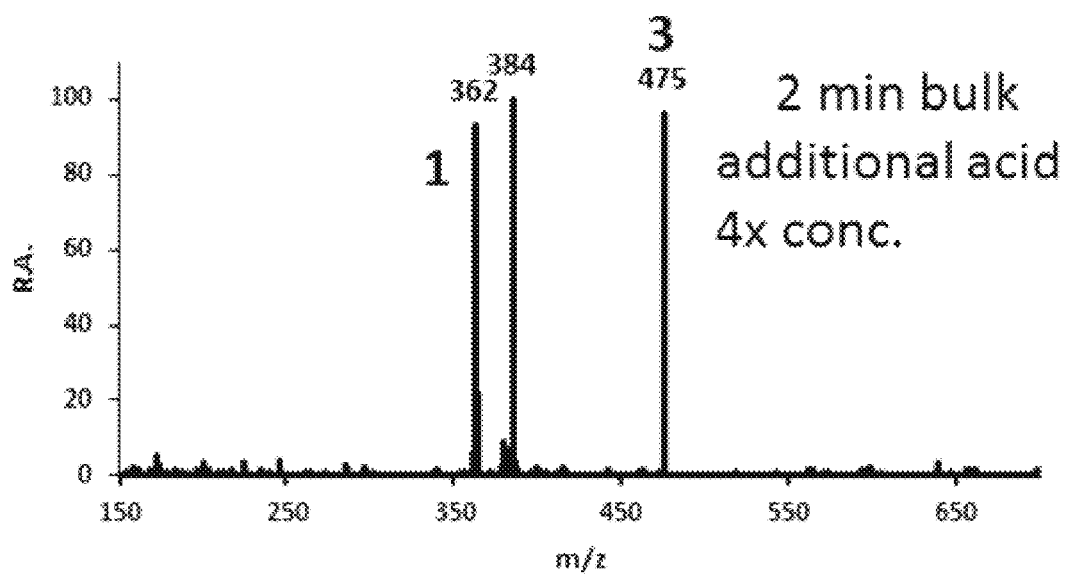
Figure 5C:
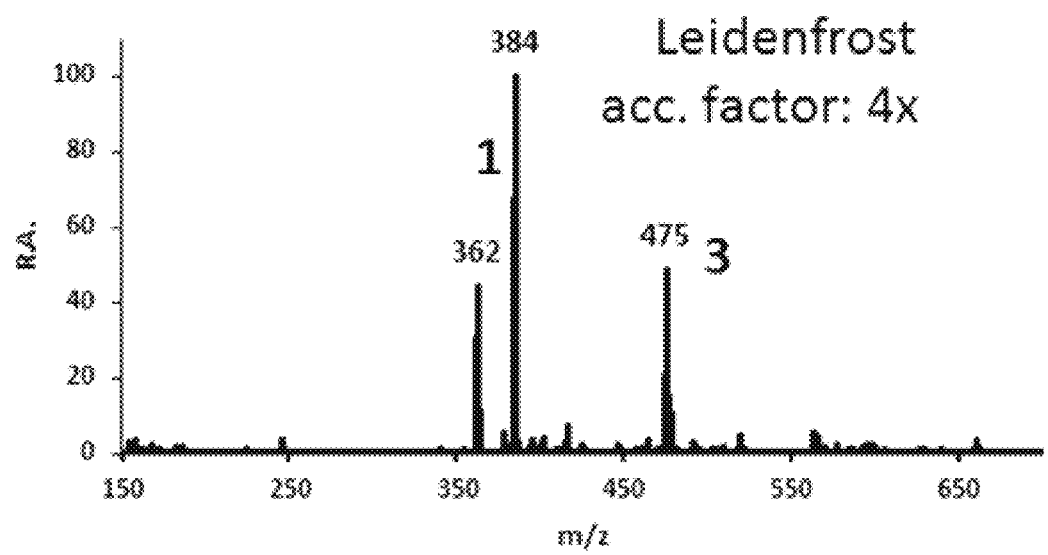
Figure 5D:
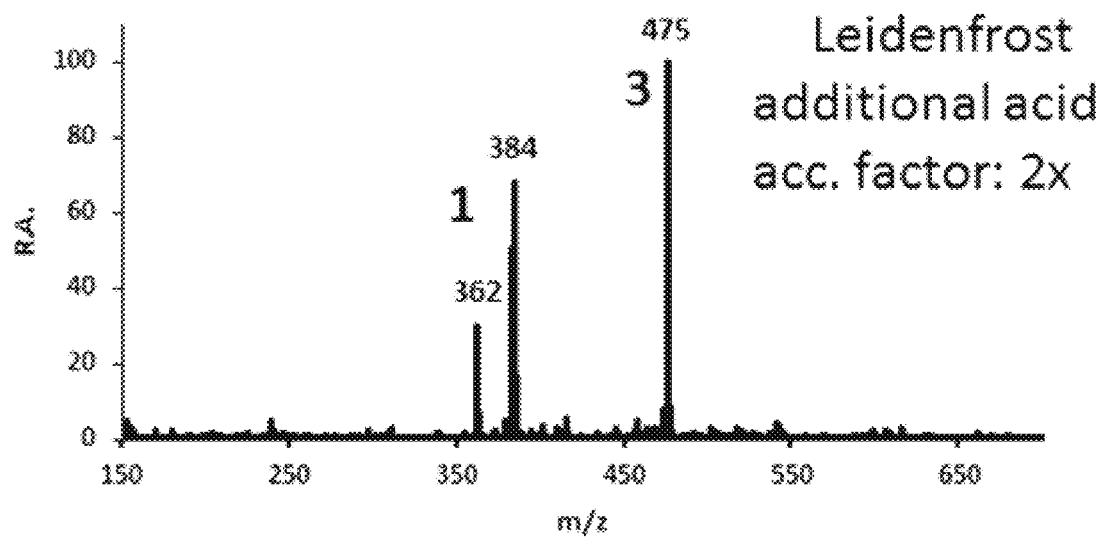

Reaction of neutral isatin (4) with phenylhydrazine (5) to form the hydrazone product (7) via a detectable pre-condensation intermediate (6) (Scheme 2) was investigated. This reaction is known to be accelerated in ESI when increasing the distance between the spray source and MS inlet, ascribed to solvent evaporation and increased concentrations and surface/volume ratio. The Leidenfrost version of this reaction also showed a substantial acceleration factor (×6 after correction for concentration effects) over the bulk phase reaction. The data are shown in Table 1 and in FIGS. 2A-B.

Scheme 2: Reaction of 4 and 5 to form the hydrazone 7 through intermediate 6.

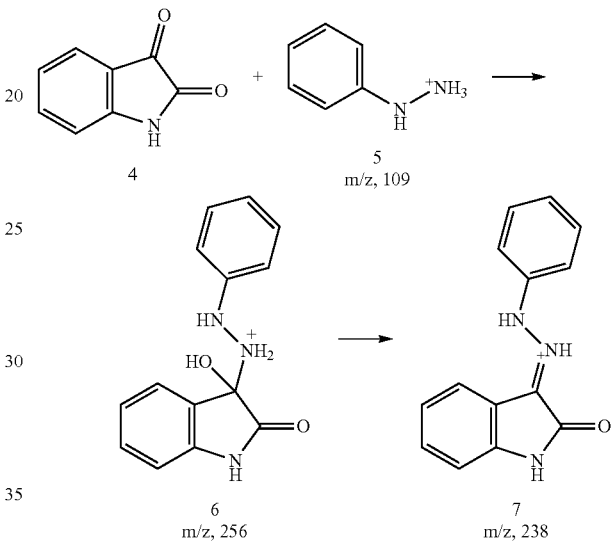

The Katritzky reaction (Scheme 3) between 2,4,6-triphenylpyrylium (8) and 4-methoxyanaline (9) to yield the corresponding pyridinium cation (10) was investigated also.

TABLE 1

Bulk-phase and Leidenfrost droplet reactions and acceleration factors (acc. factor)

| Girard T/Hydrazine Reaction Products 3/1 Ratio of ion intensities | | | | | | Phenylhydrazine/Isatin Reaction Products 7/5 Ratio of ion intensities | | | |
| --- | --- | --- | --- | --- | --- | --- | --- | --- | --- |
| Reaction time (min) | x4 | x4 add'l acid | LF Droplet | X1 Bulk | LF Droplet, add'l acid | Bulk, x1 add'l acid | Reaction time (min) | x4 conc. | LF Droplet | x1 Bulk |
| 2 | 0.1 | 0.5 | 0.4 | 0.05 | 1.0 | 0.06 | 2 | 0.05 | 0.3 | 0.03 |
| 60 | 0.6 | 2.0 | Acc. factor: 4 | | Acc. factor: 2 | | 60 | 0.1 | Acc. factor: 6 | |
| 120 | 1.0 | 2.8 | | | | | 120 | 0.2 | | |
| 180 | 3.2 | 3.4 | | | | | 180 | 0.3 | | |
| Katritsky reaction products 10/8 Ratio of ion intensities | | | | | | Claisen-Schmidt Reaction Products 13/11 Ratio of ion intensities | | | |
| Reaction time (min) | x4 conc. | x4 conc. with base | LF Droplet | x1 Bulk | LF Droplet with base | x1 Bulk with base | Reaction time (min) | x4 conc. | LF Droplet | x41 Bulk |
| 2 | 0.1 | 0.4 | 0.8 | 0.05 | 20 | 0.2 | 2 | 0.6 | 10 | 0.25 |
| 60 | 0.2 | 0.8 | Acc. factor: 8 | | Acc. factor: 50 | | 60 | 3.3 | Acc. factor: 17 | |
| 120 | 0.5 | 2.1 | | | | | 120 | 10 | | |
| 180 | 0.6 | 10 | | | | | 180 | 18 | | |

This base-catalyzed reaction again showed a strong dependence on the catalyst. The reaction had been previously investigated by paper spray ionization (thin film experiment) and it showed a significant reaction acceleration. Reaction (2 min, constant volume) in Leidenfrost droplets showed acceleration factors of 8 and 50 for the reaction performed without and with the base catalyst, respectively (FIGS. 3A-D, Table 1). Note that the time taken for the bulk reaction to reach the same product/reagent ion intensities is an alternative measure of acceleration factor. In this case it is more than 11 hour vs. 2 min.

The potential for scaling-up the Leidenfrost reactor was explored using the Katritsky reaction. In a prototype experiment, eight ceramic spacers were used to isolate eight droplets and keep them from fusing. The droplets were levitated for ca. 2 minutes while their individual volumes (0.5 mL) were maintained by addition of fresh reaction mixture. When the spacers were removed to allow the droplets to fuse, a single large droplet formed and it was immediately extracted from the surface. The resulting sample 18 mg, was analyzed by MS and found by standard addition of reagent 8 to be 90% pure (10% unconverted 8). This experiment illustrates the ease of manipulating these droplets, the ability to multiplex this meso-scale reactor system and the synthesis organic compounds on the mg scale. Example 5 below contains details of the multiplexing approach.

Scheme 3: Pyrylium cation (8) reacted with 4-methoxyanaline (9) to produce the pyridinium cation product (10).

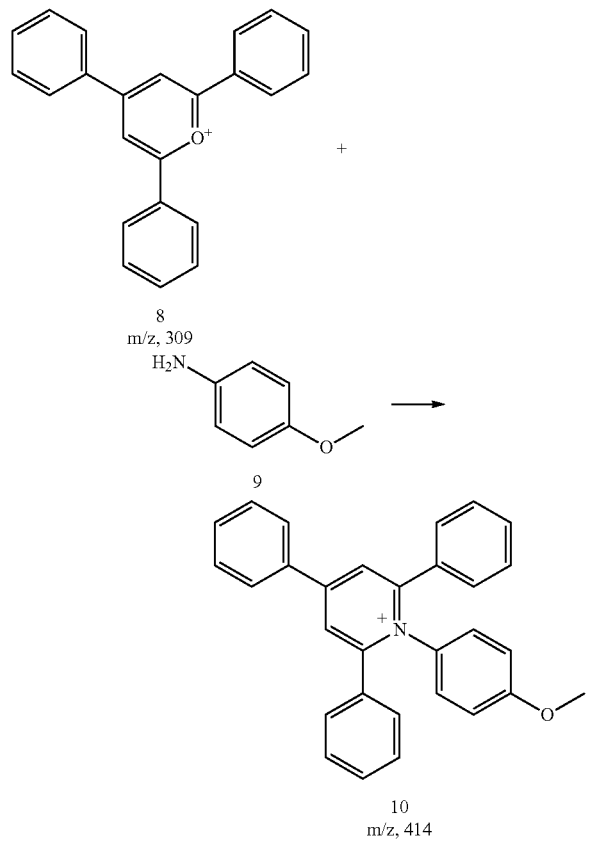

has been well-characterized by paper spray and ESI. 6-Hydroxy-1-indanone (11) was reacted with benzaldehyde (12) in the presence of base to form the condensation product (13). Both the starting material (11) and the product (13) presumably deprotonate at the aromatic hydroxyl and have similar ionization efficiencies in the negative ion mode. The mass spectra (FIGS. 4A-D) show significantly more product for the Leidenfrost experiment than for the bulk-phase reaction (17× acceleration factor).

In order to explore the role of the surface on Leidenfrost droplet acceleration, a surfactant was added to reaction mixture. Addition of Triton-x-100:

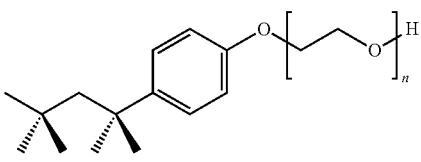

in varied amounts showed significant effects on the reaction acceleration. Addition of 0.01% (v/v) triton showed no effect but 1% (v/v) triton containing reaction mixture, when subject to the same Leidenfrost conditions, showed significant suppression of acceleration (FIGS. 4A-D) while 5% (v/v) triton suppressed the reaction to bulk values. Higher concentrations of triton would not allow the droplet to be maintained at the Leidenfrost temperature. This experiment demonstrates the role of the surface in the acceleration of these reactions since small concentrations of triton block the surface and diminish accelerated product formation. Further details on the roles of concentration and Leidenfrost methods can be found in Example 6 below.

Scheme 4: Condensation of 11 and 12 to form the product 13 examined in the negative ion mode.

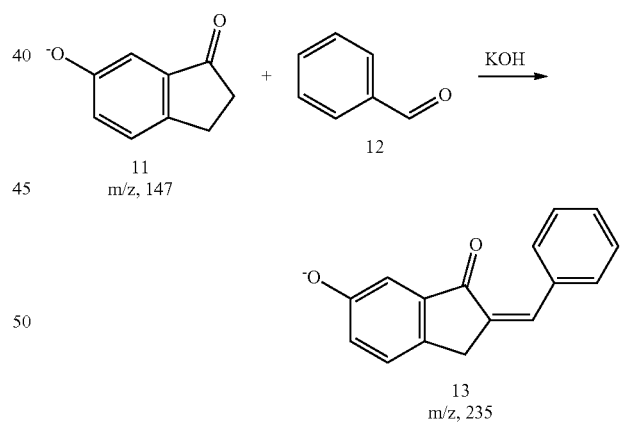

Lastly, the Claisen-Schmidt base-catalyzed condensation was investigated because the acceleration of this reaction Acceleration of a variety of chemical reactions in Leidenfrost droplets has been demonstrated. By controlled additions of reaction mixture to the droplet and comparison bulk-phase reactions the acceleration phenomenon is shown to be due mainly to interfacial reactivity, although concentration effects do play a role as detailed in in the Examples. Surfactant addition experiments confirm the role of surface activity in the accelerated reactions which in this respect are similar to the reaction acceleration seen in spray-based microdroplets. The methods of the invention may be used to screen reactions and create milligram quantities of material in minutes.

As mentioned herein, analyzing the reaction product can be by mass spectrometry, however, any analytical technique, such as liquid chromatography, UV analysis, ELSD analysis, optical spectroscopy, etc., can be used. The following sections discuss analysis by mass spectrometry.

Ion Traps and Mass Spectrometers

Any mass spectrometer (e.g., bench-top mass spectrometer of miniature mass spectrometer) may be used to analyze reaction products from methods of the invention and in certain embodiments the mass spectrometer is a miniature mass spectrometer. An exemplary miniature mass spectrometer is described, for example in Gao et al. (Anal. Chem. 2008, 80, 7198-7205.), the content of which is incorporated by reference herein in its entirety. In comparison with the pumping system used for lab-scale instruments with thousands of watts of power, miniature mass spectrometers generally have smaller pumping systems, such as a 18 W pumping system with only a 5 L/min (0.3 m$^3$/hr) diaphragm pump and a 11 L/s turbo pump for the system described in Gao et al. Other exemplary miniature mass spectrometers are described for example in Gao et al. (Anal. Chem., 2008, 80, 7198-7205.), Hou et al. (Anal. Chem., 2011, 83, 1857-1861.), and Sokol et al. (Int. J. Mass Spectrom., 2011, 306, 187-195), the content of each of which is incorporated herein by reference in its entirety.

In certain embodiments, a Discontinuous Atmospheric Pressure Interface (DAPI) can be utilized with the mass spectrometer. A DAPI is particularly useful when coupled to a miniature mass spectrometer, but can also be used with a standard bench-top mass spectrometer. Discontinuous atmospheric interfaces are described in Ouyang et al. (U.S. Pat. No. 8,304,718 and PCT application number PCT/US2008/065245), the content of each of which is incorporated by reference herein in its entirety.

Any ion trap known in the art can be used in systems of the invention. Exemplary ion traps include a hyperbolic ion trap (e.g., U.S. Pat. No. 5,644,131, the content of which is incorporated by reference herein in its entirety), a cylindrical ion trap (e.g., Bonner et al., International Journal of Mass Spectrometry and Ion Physics, 24(3):255-269, 1977, the content of which is incorporated by reference herein in its entirety), a linear ion trap (Hagar, Rapid Communications in Mass Spectrometry, 16(6):512-526, 2002, the content of which is incorporated by reference herein in its entirety), and a rectilinear ion trap (U.S. Pat. No. 6,838,666, the content of which is incorporated by reference herein in its entirety).

Ionization Sources

For mass spectrometry analysis, the reaction product is typically first ionized. Any type of ionizing source known in the art may be used, and the source used will depend, at least in part, on the reaction product to be analyzed. Exemplary mass spectrometry techniques that utilize ionization sources at atmospheric pressure for mass spectrometry include paper spray ionization (ionization using wetted porous material, Ouyang et al., U.S. patent application publication number 2012/0119079), electrospray ionization (ESI; Fenn et al., Science, 1989, 246, 64-71; and Yamashita et al., J. Phys. Chem., 1984, 88, 4451-4459.); atmospheric pressure ionization (APCI; Carroll et al., Anal. Chem. 1975, 47, 2369-2373); and atmospheric pressure matrix assisted laser desorption ionization (AP-MALDI; Laiko et al. Anal. Chem., 2000, 72, 652-657; and Tanaka et al. Rapid Commun. Mass Spectrom., 1988, 2, 151-153,). The content of each of these references is incorporated by reference herein in its entirety.

Exemplary mass spectrometry techniques that utilize direct ambient ionization/sampling methods include desorption electrospray ionization (DESI; Takats et al., Science, 2004, 306, 471-473, and U.S. Pat. No. 7,335,897); direct analysis in real time (DART; Cody et al., Anal. Chem., 2005, 77, 2297-2302.); atmospheric pressure dielectric barrier discharge Ionization (DBDI; Kogelschatz, Plasma Chemistry and Plasma Processing, 2003, 23, 1-46, and PCT international publication number WO 2009/102766), and electrospray-assisted laser desorption/ionization (ELDI; Shiea et al., J. Rapid Communications in Mass Spectrometry, 2005, 19, 3701-3704.). The content of each of these references in incorporated by reference herein its entirety.

On-Line Reaction Monitoring

In certain embodiments, monitoring of the reaction, in real-time, may be desirable. Accordingly, certain embodiments utilize on-line reaction monitoring systems for monitoring the formation of a reaction product within a Leidenfrost-levitated droplet. The volume of the droplet is maintained as discussed above and the rate/amount of addition of solvent or reagents is determined by the rate and/or amount of liquid removed from the Leidenfrost-levitated droplet in which the reaction is occurring. The removed portion of liquid is directly transferred to the on-line reaction monitoring system. The system may be equipped with a transfer line that couples to the to the Leidenfrost-levitated droplet in which the reaction is occurring.

An exemplary on-line reaction monitoring system is described for example in Cooks et al. (U.S. Pat. No. 9,500,623), the content of which is incorporated by reference herein in its entirety. Briefly, a transfer line is positioned in proximity to the Leidenfrost-levitated droplet in which the reaction is occurring or the reaction in the Leidenfrost-levitated droplet is conducted inside a pressurized vessel to which the transfer line is connected. A portion of the Leidenfrost-levitated droplet in which the reaction is occurring is transferred through the transfer line to an emitter-spray tip. Ionization may be produced by inductive electrospray ionization. A positive electrospray potential applied to an electrode near to but not in physical contact with the solution being sprayed or the emitter is pulsed repeatedly to produce strong electric fields of both polarities which result in bursts of charged droplets being emitted from the solution while avoiding direct physical contact between the high voltage and the reaction solution. Sheath gas may be used to help in the nebulization process and minimize size-variation in the droplets. Sample splitting was useful in accelerating the flow rate of sampling and decreasing the delay time while avoiding contamination of the MS inlet. Mass spectra recorded as a function of time give the desired kinetic information.

Ion Transfer

In certain embodiments, ionization of a reaction product within a Leidenfrost-levitated droplet may be desirable at the location where the Leidenfrost-levitated droplet resides. In such embodiments, the generated reaction product ions may be transferred using an ion transfer line to an analysis system, such as a mass spectrometer. Systems and methods of transferring ions are described, for example in Ouyang et al. (U.S. Pat. No. 8,410,431), the content of which is incorporated by reference herein in its entirety. Such devices generate a laminar gas flow that allows for efficient transfer of ions without significant loss of signal intensity over longer distances, such as distances of at least about 5 cm, at least about 10 cm, at least about 20 cm, at least about 50 cm, at least about 100 cm, at least about 500 cm, at least about 1 m, at least about 3 m, at least about 5 m, at least about 10 m, and other distances. Ion transfer devices of the invention are useful for chemical analysis in situations in which it is important for the ion focusing device or instrument and the object being examined to be in different locations. Generally, the ion transfer member is operably coupled to a gas flow generating device, in which the gas flow generating device produces a laminar gas flow that transfers the gas phase ions to an inlet of the ion focusing device.

Ion transfer devices of the invention provide enlarged flow to carry ions from a distant sample to the ion focusing device. The basic principle used in the transport device is the use of the gas flow to direct gas and ions into the ion transfer member and to form a laminar flow inside the ion transfer member to keep the ions away from the walls while transferring the gas and ions through the ion transfer member. The analyte ions of interest are sampled at some point downstream along the ion transfer member. The laminar flow is achieved by balancing the incoming and outgoing gas flow. Thus recirculation regions and/or turbulence are avoided. Thus, the generated laminar flow allows for high efficient ion transport over long distance or for sampling of ions over large areas.

Ion transfer devices of the invention also provide enlarged flow to carry ions from the ion source to the ion focusing device. Additional gas flow provided by a miniature sample pump connected with the ion transfer member facilitates ion transfer from an ambient ionization source to the vicinity of the ion focusing device.

As described in certain embodiments, an ion transfer member, e.g., a tube with an inner diameter of about 10 mm or greater, may be used to transfer ions from the ionization source to the ion focusing device. The larger opening of the ion transfer member, as compared to the opening of the inlet of the ion focusing device, is helpful for collection of sample ions generated in a large space, e.g. on a surface of large area. The large flow conductance of the ion transfer member allows the gas carrying ions to move toward the inlet of the ion analysis device at a fast flow rate. The ion transfer member is coupled to a gas flow generating device. The gas flow generating device produces a gas flow inside the ion transfer member. The inlet of the ion analysis device receives the ions transferred from the ambient ionization source.

The ion transfer member may be any connector that allows for production of a laminar flow within it and facilitates transfer of ions without significant loss of ion current. Exemplary ion transfer members include tubes, capillaries, covered channels, open channels, and others. In a particular embodiment, the ion transfer member is a tube. The ion transfer member may be composed of rigid material, such as metal or glass, or may be composed of flexible material such as plastics, rubbers, or polymers. An exemplary flexible material is TYGON tubing.

The ion transfer member may be any shape as long the shape allows for the production of a flow to prevent the ions from reaching the internal surfaces of the ion transfer member where they might become neutral. For example, the ion transfer member may have the shape of a straight line. Alternatively, the ion transfer member may be curved or have multiple curves.

The ion transfer member is coupled to a gas flow generating device. The gas flow generating device is such a device capable of generating a gas flow through the ion transfer member. The gas flow generating device facilitates transfer of the ions from the ambient ionization source to the inlet of the ion analysis device. In certain embodiments, the gas flow generating device is a pump with a high flow rate and a low compression ratio. An example of such a pump is that found in a shop vacuum or a small sample pump. The proper pumps used for the coupling are different from those used for a mass spectrometer, e.g. a rotary vane pump or a turbo molecular pump, which pumps have a high compression ratio. The high compression ratio pumps of a mass spectrometer cannot be connected to the atmosphere through an opening of the conductance described here. For example, Cotte-Rodriguez et al. (Chem. Commun., 2006, 2968-2970) describe a set-up in which the inlet of the mass spectrometer was elongated and gas flow generated by the pump inside a mass spectrometer was used to transfer ions over a distance up to 1 m. The ions were transferred from the atmosphere to a region at about 1 torr. A significant loss in signal occurred for the transfer of the ions using the set-up described in Cotte-Rodriguez, and ions generated over a large area could not be efficiently collected into the inlet.

In other embodiments, the gas flow generating device is the ambient ionization source. For example, a source used for desorption electrospray ionization (DESI) generates a gas flow sufficient to produce a laminar flow through the ion transfer member, and thus produces a laminar gas flow that transfers the gas phase ions over a long distance to an inlet of the ion analysis device.

Numerous additional devices may be coupled with the ion transfer member to further facilitate transfer of the ions from the ambient ionization source to the inlet of the ion focusing device. For example, an electric lens may be used to focus the ions toward the center of the ion transfer member while the gas flow generating device pumps away neutral gases. In other embodiments, an electro-hydrodynamic lens system may be implemented to use the air dynamic effects to focus the heavier particles and to use the electric field to focus the charged particles toward the center of the ion transfer member.

In other embodiments, a distal end of the ion transfer member may include a plurality of inlets for transferring ions from multiple locations to the inlet of the ion focusing device. In still other embodiments, the ion transfer member includes additional features to prevent ions from being adsorbed onto the inside wall. For example, a dielectric barrier discharge (DBD) tubing is made from a double stranded speaker wire. The insulator of the wire serves as the dielectric barrier and the DBD occurs when high voltage AC is applied between the two strands of the wire. The DBD inside the tube prevents the ions from adsorbing onto the wall and provide a charge-enriched environment to keep the ions in the gas phase. This DBD tube can also be used for ionizing the gas samples while transferring the ions generated to the inlet of the ion focusing device. The DBD tube can also be used for ion reactions while transferring the ions generated to the inlet of the ion focusing device.

Collection of Reaction Product without or after Mass-Selective Analysis

In certain embodiments, it may be desirable to collect the reaction product from the Leidenfrost-levitated droplet without or after mass-selective analysis. Systems and methods for collecting ions that have been analyzed by a mass spectrometer are shown in Cooks, (U.S. Pat. No. 7,361,311), the content of which is incorporated by reference herein in its entirety. In another embodiment, reaction product may be collected without mass analysis (See U.S. Pat. No. 9,184,038, the content of which is incorporated by reference herein in its entirety). The collected reaction product may then be subsequently analyzed by any suitable technique, such as infrared spectrometry or mass spectrometry.

Generally, the preparation of microchips arrays of metal ions first involves the ionization of the metal. The metal ions can be produced by any of the methods discussed above. The ions can then be focused and collected using methods described below or can first be separated based on their mass/charge ratio or their mobility or both their mass/charge ratio and mobility. For example, the ions can be accumulated in an ion storage device such as a quadrupole ion trap (Paul trap, including the variants known as the cylindrical ion trap and the linear ion trap) or an ion cyclotron resonance (ICR) trap. Either within this device or using a separate mass analyzer (such as a quadrupole mass filter or magnetic sector or time of flight), the stored ions are separated based on mass/charge ratios. Additional separation might be based on mobility using ion drift devices or the two processes can be integrated. The separated ions are then deposited on a microchip or substrate at individual spots or locations in accordance with their mass/charge ratio or their mobility to form a microarray.

Whether or not mass-selection is used, the microchip or substrate is moved or scanned in the x-y directions and stopped at each spot location for a predetermined time to permit the deposit of a sufficient number of molecules to form a spot having a predetermined density. Alternatively, the gas phase ions can be directed electronically or magnetically to different spots on the surface of a stationary chip or substrate. The molecules are preferably deposited on the surface with preservation of their structure, that is, they are soft-landed.

In embodiments in which ions are collected without prior separation, the collection surface is operably coupled to receive the spray including the ions, as illustrated in FIG. 1. In embodiments that first use mass-selection, the surface is located behind the detector assembly of the mass spectrometer. In embodiments that use an ion focusing device, the surface for ion landing is located after the ion focusing device.

In embodiments that use mass-selection prior to ion landing, the high voltages on the conversion dynode and the multiplier are turned on and the ions are detected to allow the overall spectral qualities, signal-to-noise ratio and mass resolution over the full mass range to be examined. In the ion-landing mode, the voltages on the conversion dynode and the multiplier are turned off and the ions are allowed to pass through the hole in the detection assembly to reach the landing surface of the plate (such as a gold plate). The surface is grounded and the potential difference between the source and the surface is 0 volts.

An exemplary substrate for soft landing is a gold substrate (20 mm×50 mm, International Wafer Service). This substrate may consist of a Si wafer with 5 nm chromium adhesion layer and 200 nm of polycrystalline vapor deposited gold. Before it is used for ion landing, the substrate is cleaned with a mixture of $H_2SO_4$ and $H_2O_2$ in a ratio of 2:1, washed thoroughly with deionized water and absolute ethanol, and then dried at 150° C. A Teflon mask, 24 mm×71 mm with a hole of 8 mm diameter in the center, is used to cover the gold surface so that only a circular area with a diameter of 8 mm on the gold surface is exposed to the ion beam for ion soft-landing of each mass-selected ion beam. The Teflon mask is also cleaned with 1:1 MeOH:$H_2O$ (v/v) and dried at elevated temperature before use. The surface and the mask are fixed on a holder and the exposed surface area is aligned with the center of the ion optical axis. Any period of time may be used for landing of the ions. In mass-selection embodiments, between each ion-landing, the instrument is vented, the Teflon mask is moved to expose a fresh surface area, and the surface holder is relocated to align the target area with the ion optical axis. After soft-landing, the Teflon mask is removed from the surface.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Reaction Procedures

Girard's Reagent T/Cortisone Hydrazone Formation

Reactions were performed by adding 2 mL of a Girard's reagent T, (1 mM in 80:19.5:0.5 (v/v/v), methanol:water:formic acid) solution to 2 mL of a cortisone (1 mM 80:20 (v/v), methanol:water) solution (Scheme 1). Half of this sample was used for the Leidenfrost experiment while the other half was used for the comparative bulk-phase experiment so that the solutions have the same starting concentrations. Samples prepared at 4× concentrations were prepared in the same manner, but to 4 mM rather than 1 mM concentrations.

Additional acid experiments were performed using the same reagents previously mentioned with 1:10 formic acid in methanol in a 1:1:1 ratio with the other two reagents. 4× concentration experiments in this case used the same amount of acid and simply a greater concentration of the reagents.

Phenylhydrazine/Isatin Hydrazone Formation

Combine 4 mL of 3 mM methanolic isatin with 40 uL phenylhydrazine and 4 uL 1 M HCl (methanol) (Scheme 2). For the 4× concentration solutions all reagent concentrations were increased by a factor of four.

Katritzky Reaction

To 3 mL of 2,4,6-triphenylpyrilium (5 mM in acetonitrile) was added 1.9 mL of 4-anisidine (8 mM in acetonitrile) (Scheme 3). This reaction was also performed with base in the same way but with the addition of 20 uL of 1.8 M methanolic potassium hydroxide. Bulk-phase reactions were performed at these concentrations and 4× concentrations. 4× concentration data was obtained using 20 mM 2,4,6-triphenylpyrilium, 32 mM 4-anisidine, and by adding 80 uL of 1.8 M methanolic potassium hydroxide.

Claisen-Schmidt Base-Catalyzed Condensation

This reaction was performed by mixing 2 mL 50 mM benzaldehyde (in methanol), 2 mL 50 mM 6-hydroxy-1-indanone (in methanol) and 2 mL 1.8 mM methanolic potassium hydroxide (Scheme 4). Reactions at 4× concentration were performed using 4× the concentration of the reagents and 4× the base.

Triton experiments with this reaction were performed by mixing the triton with the 6-hydroxy-1-indanone and then adding the aldehyde and base.

Example 2: Determination of Acceleration Factor

Acceleration factors are used throughout this application and are calculated using ratios of reaction product/starting material for the Leidenfrost conditions vs. bulk. Since the Leidenfrost droplets are thought to have the same or greater acceleration compared to the bulk-phase solution we have chosen to represent the factor as the ratio of Leidenfrost droplets ratio at a given time (t=2 mins) over the ratio of product/starting material of the bulk-phase reaction at the same time. This ratio of ratios adjusts for the inherent variations in ionization efficiencies for some of these reactions.

The approximations are extremely conservative estimates of the acceleration factor. More significant values could be attained in ratio of times would be used by comparing the 2 mins it takes to create a significant product yield and correlate that to the amount of time it takes to create the same product yield in the bulk-phase. In some cases, similar acceleration factors are achieved and in others significantly greater acceleration factors can be seen. For example, the first reaction explored, the reaction of Girard T with cortisone can take 2 hours to create product but a similar amount of product can be created in 2 minutes via the Leidenfrost experiments.

Example 3: nESI-MS Analysis

All mass analyses were performed using nanoESI-MS. The distance between the tip of the spray emitter and ion transfer capillary to the MS was held constant at ca. 1 mm. Experiments were performed using borosilicate glass pulled to a ca. 5 um opening. A spray voltage of either positive or negative 1.5 kV was used for all analysis. All samples were diluted at least 100-fold prior to mass analysis with either acetonitrile or methanol. Positive ion mode was used for all chemical analysis except for analysis for the Claisen-Schmidt base-catalyzed condensation samples which used negative ion mode.

Example 4: Girard T/Cortisone Reaction Spectra

Acceleration factors measuring the product/reagent ratios with the 5 mM bulk concentrations would be 17; however, the concentration increase in the Leidenfrost droplets due to evaporation must be taken into account. This was done by measuring the bulk reaction data measured at four times the initial concentration. Hydrazone formation from the Leidenfrost droplets then shows a product (3)/reagent (1) ion ratio which is notably higher (factor of 4) than that for the bulk solution (FIGS. 5A-D).

Example 5: Scale-Up

Figure 6:
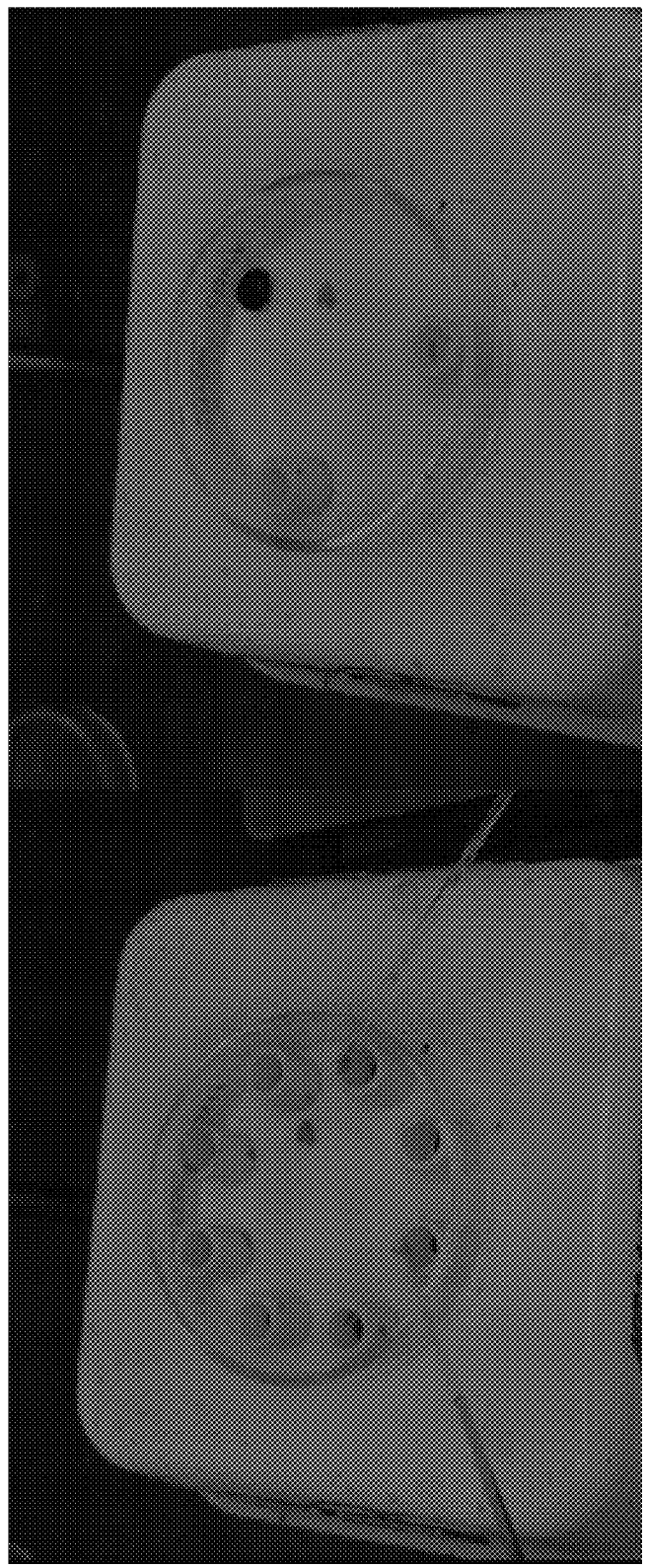
FIG. 6 shows photographs of a multiplexing approach where the separated Leidenfrost droplets are continually replenished with reaction mixture (left) and when the reaction had run for ca. 2 mins and all but two of the droplet spacers have been removed allowing the droplets to fuse prior to collection (right).

FIG. 6 shows photographs of a multiplexing approach where the separated Leidenfrost droplets are continually replenished with reaction mixture (left) and when the reaction had run for ca. 2 mins and all but two of the droplet spacers have been removed allowing the droplets to fuse prior to collection (right).

Example 6: Effect Concentration and Leidenfrost Effect

Figure 7A:
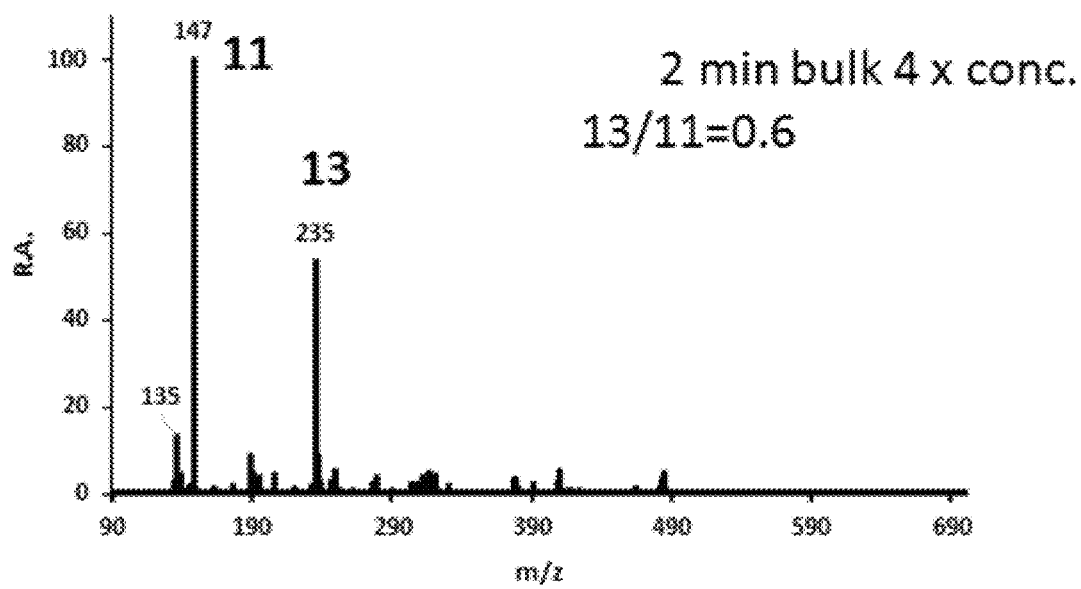
FIG. 7A shows bulk-phase at 4× concentration after 2 mins.
Figure 7B:
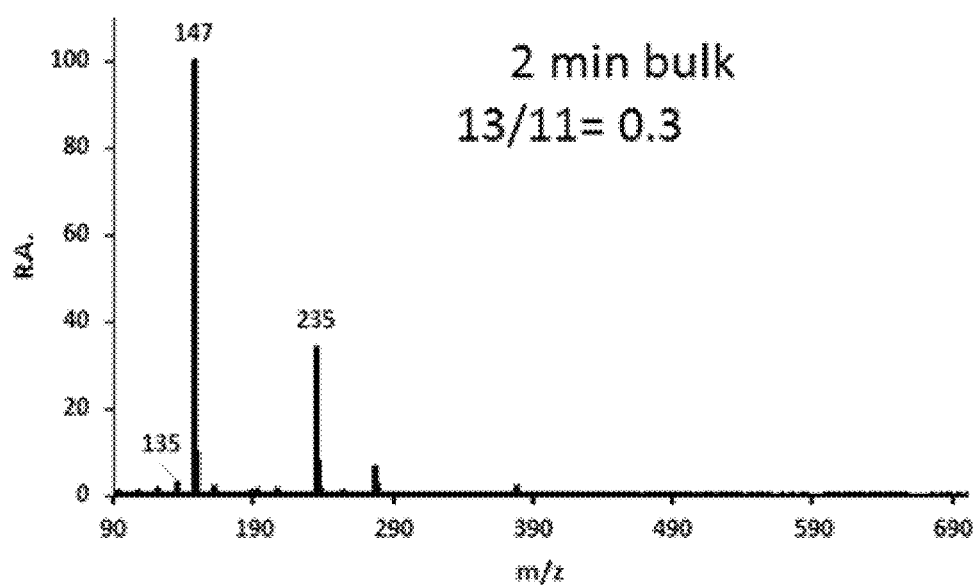
FIG. 7B shows bulk-phase at standard concentrations.
Figure 7C:
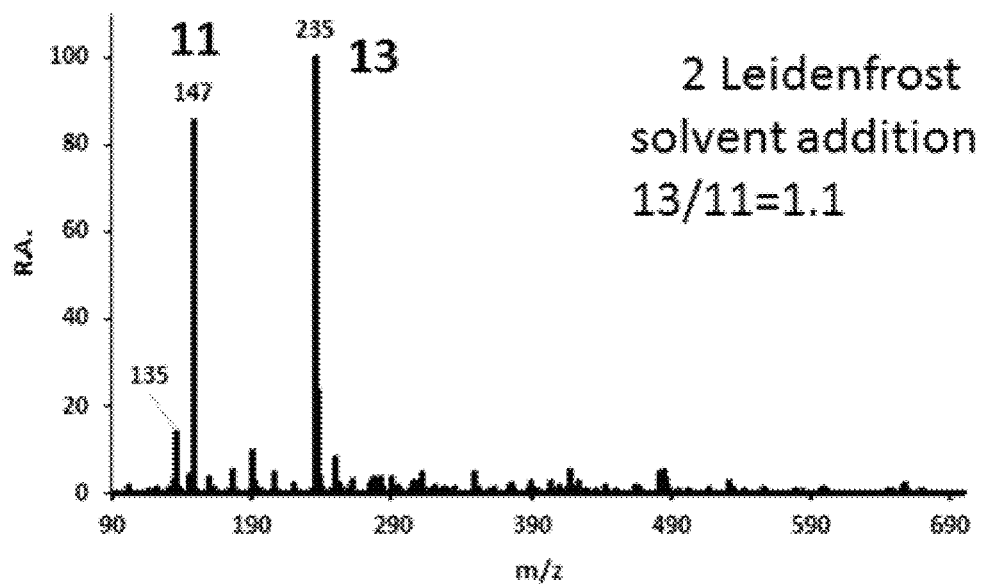
FIG. 7C shows Leidenfrost droplet with solvent added and not the traditional reaction mixture addition.
Figure 7D:
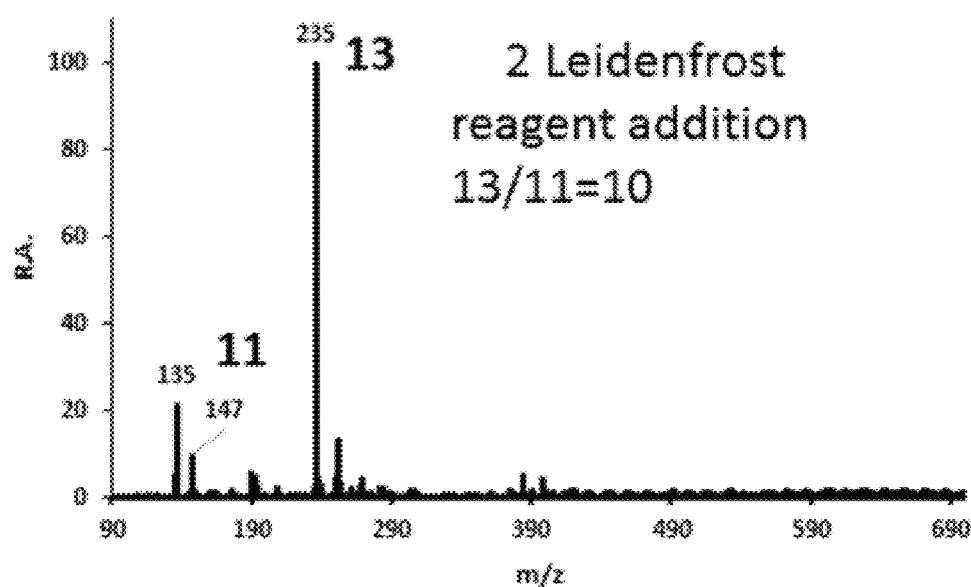
FIG. 7D shows the Leidenfrost droplet with reaction mixture addition.

Exploring the effect of concentration on both bulk-phase reactions and reactions performed in the Leidenfrost experiments was important to decoupling the sources of acceleration (FIG. 6). For simplicity all reactions were performed for two minutes. Considering the case of the Katritsky reaction, the enhancement in bulk due simply to an increase in concentration of 4× was found to be a factor of two (0.6/0.3), FIGS. 7A-B. Simply adding solvent to the Leidenfrost droplet and maintaining constant Leidenfrost volume without adding reaction mixture provided an acceleration of 4 (over the low concentration 2 min bulk), which can be fully attributed to the Leidenfrost effect. Adding reaction mixture rather than solvent saw an acceleration factor of 17 over the 4× concentrated sample and 33 over the simple bulk in FIG. 6 (right panel). These findings and the surfactant findings discussed above illustrate that the roles of both concentration and surface effects are important in causing reaction acceleration in the Leidenfrost effect. This is similar to previous findings on reaction acceleration in ESI.

What is claimed is:

1. A method for forming and collecting a reaction product, the method comprising conducting a reaction within a Leidenfrost-levitated droplet while maintaining a substantially constant volume of the Leidenfrost-levitated droplet, thereby forming a reaction product within the Leidenfrost-levitated droplet; and
collecting the reaction product in the Leidenfrost-levitated droplet without evaporating the Leidenfrost-levitated droplet.

2. The method according to claim 1, further comprising analyzing the reaction product.

3. The method according to claim 2, wherein analyzing is by a mass spectrometry technique.

4. The method according to claim 1, wherein maintaining the substantially constant volume comprises introducing droplets of pure solvent or the reaction mixture to the Leidenfrost-levitated droplet.

5. The method according to claim 1, wherein the method further comprises conducting multiple reactions in multiple separate Leidenfrost-levitated droplets.

6. The method according to claim 5, wherein the multiple separate Leidenfrost-levitated droplets are merged with each other.

7. The method according to claim 5, wherein the multiple reactions are the same.

8. The method according to claim 5, wherein the multiple reactions are different.

9. The method according to claim 1, wherein the method is conducted without the use of surfactants.

10. A method for forming and collecting a reaction product, the method comprising:
introducing a first liquid droplet onto a heated surface that is at a temperate that is at or above a Leidenfrost point of the first liquid such that the first liquid droplet levitates on the heated surface, wherein the first liquid droplet comprises reagents for a reaction;
conducting a reaction in the first liquid droplet using the reagents in order to form a reaction product;
introducing one or more subsequent liquid droplets to the first liquid droplet on the heated surface such that the one or more subsequent liquid droplets merge with the first liquid droplet; and
collecting the reaction product in the first liquid droplet without evaporating the first liquid droplet.

11. The method according to claim 10, further comprising analyzing the reaction product.

12. The method according to claim 11, wherein analyzing is by a mass spectrometry technique.

13. The method according to claim 10, wherein the first liquid droplet is maintained at a substantially constant volume throughout the method.

14. The method according to claim 10, wherein the one or more subsequent liquid droplets each comprise the reagents for the reaction.

15. The method according to claim 10, wherein the method is conducted without the use of surfactants.

16. A method for forming and collecting a reaction product, the method comprising:
   conducting a reaction within a Leidenfrost-levitated droplet, thereby forming a reaction product within the Leidenfrost-levitated droplet; and
   collecting the reaction product in the Leidenfrost-levitated droplet without evaporating the Leidenfrost-levitated droplet.

17. The method according to claim 16, wherein the droplet reduces in volume as the reaction occurs.

18. The method according to claim 16, wherein a rate of the reaction is accelerated as compared to a rate of the reaction conducted outside of the Leidenfrost-levitated droplet.

\* \* \* \* \*